(12) United States Patent
Watanabe

(10) Patent No.: US 12,383,211 B2
(45) Date of Patent: Aug. 12, 2025

(54) X-RAY CT APPARATUS AND ATTACHING METHOD AND DETACHING METHOD OF UNITS WITHIN GANTRY OF X-RAY CT APPARATUS

(71) Applicant: CANON MEDICAL SYSTEMS CORPORATION, Tochigi (JP)

(72) Inventor: Takahito Watanabe, Nasushiobara (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 404 days.

(21) Appl. No.: 18/157,189

(22) Filed: Jan. 20, 2023

(65) Prior Publication Data

US 2023/0233160 A1    Jul. 27, 2023

(30) Foreign Application Priority Data

Jan. 24, 2022 (JP) ................... 2022-008429

(51) Int. Cl.
*A61B 6/03* (2006.01)
*A61B 6/00* (2006.01)
*A61B 6/40* (2024.01)

(52) U.S. Cl.
CPC ............ *A61B 6/032* (2013.01); *A61B 6/4007* (2013.01); *A61B 6/4405* (2013.01); *A61B 6/4411* (2013.01)

(58) Field of Classification Search
CPC ........ A61N 5/1081; A61N 5/01; A61B 6/035; A61B 6/032; A61B 6/4014; A61B 6/4452; A61B 6/447; A61B 6/4021; A61B 6/4429
See application file for complete search history.

(56) References Cited

U.S. PATENT DOCUMENTS

| 7,447,294 | B2 | 11/2008 | Sadotomo et al. |
| 8,130,900 | B2 | 3/2012 | Luecke et al. |
| 2007/0053479 | A1 | 3/2007 | Sadatomo et al. |
| 2010/0025590 | A1 | 2/2010 | Luecke et al. |

FOREIGN PATENT DOCUMENTS

| CN | 114173666 A | * | 3/2022 | ............. A61B 6/035 |
| JP | 2007-37873 A | | 2/2007 | |
| JP | 2007-130119 A | | 5/2007 | |

* cited by examiner

*Primary Examiner* — Don K Wong
(74) *Attorney, Agent, or Firm* — Oblon, McClelland, Maier & Neustadt, L.L.P.

(57) ABSTRACT

An X-ray Computed Tomography (CT) apparatus according to an embodiment includes a gantry. The gantry includes: a rotating base rotatably supported; a plurality of units fixed to the rotating base; and a fixing member that is separately provided, is positioned apart from the rotating base, and is configured to fix at least two of the plurality of units with each other.

12 Claims, 7 Drawing Sheets

X-RAY CT APPARATUS AND ATTACHING METHOD AND DETACHING METHOD OF UNITS WITHIN GANTRY OF X-RAY CT APPARATUS

CROSS-REFERENCE TO RELATED APPLICATIONS

This application is based upon and claims the benefit of priority from Japanese Patent Application No. 2022-008429, filed on Jan. 24, 2022; the entire contents of which are incorporated herein by reference.

FIELD

Embodiments described herein relate generally to an X-ray Computed Tomography (CT) apparatus and an attaching method and a detaching method of units within a gantry of an X-ray CT apparatus.

BACKGROUND

Rotation speeds of gantries in X-ray Computed Tomography (CT) apparatuses are getting faster year by year. For example, a gantry may include a rotating base (a rotating member) that has a drum shape (a circular cylindrical shape). Provided inside the drum-shaped rotating base are a plurality of units. In the present example, the plurality of units denote, for instance, an X-ray tube, a heat exchanger (a cooling device) for the X-ray tube, a starter unit for rotating a positive pole (a target) of the X-ray tube, an X-ray detector, a high-voltage generating device, and the like. When the rotation speed of the gantry becomes higher, the magnitude of centrifugal force applied to the plurality of units becomes larger. For this reason, when the drum-shaped rotating base is structured to have high rigidity, the mass of the rotating base tends to be larger.

When the mass of the drum-shaped rotating base becomes larger, the electric energy required to rotate the rotating base also becomes larger.

Further, a technique is also known by which a frame configured to support the units is attached to a lateral face of the rotating base. However, according to this technique, large centrifugal force occurring from high-speed rotation is applied to the units. For this reason, to increase the rigidity of the frame and the rotating base to which the frame is attached, the size and the mass of the frame and the rotating base become larger. Further, in order to supplement insufficiency of an mAs value caused by the high-speed rotation, the size and the mass of the units have, generally speaking, a tendency to be large. For these reasons, it is difficult to use this technique for reducing the weight of a rotating part, while increasing the rigidity thereof so as to withstand the high-speed rotation.

Consequently, there is a demand for reducing the weight and increasing the rigidity of the entirety of a rotating part including a rotating base.

DETAILED DESCRIPTION

Figure 1:
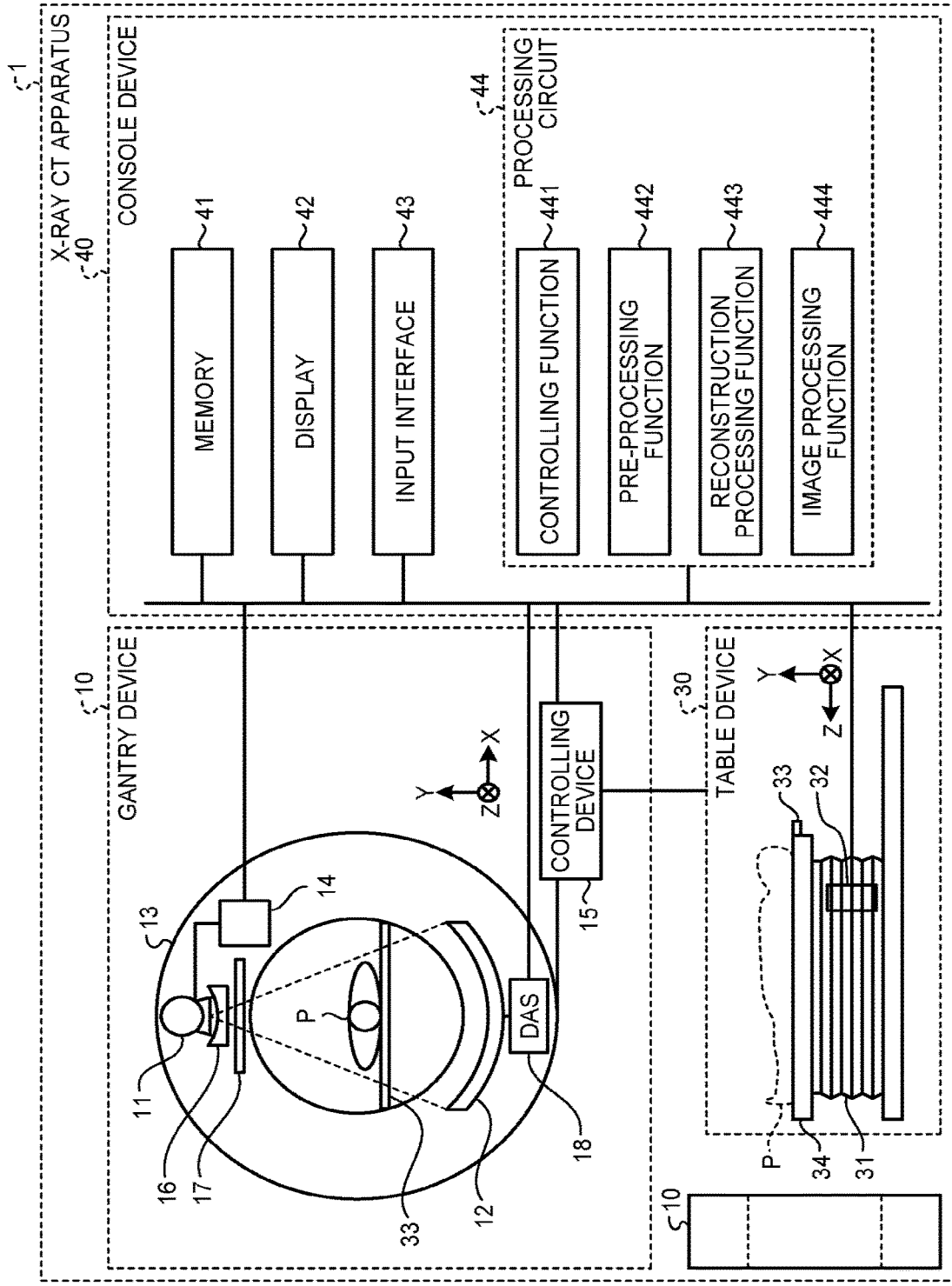
FIG. 1 is a diagram illustrating an exemplary configuration of an X-ray CT apparatus according to a first embodiment.

One of the problems to be solved by the embodiments disclosed in the present disclosure is to reduce weight and increase rigidity of the entirety of a rotating part including a rotating base. However, possible problems that can be solved by the embodiments of the present disclosure are not limited to the problem described above. It is also possible to consider the problems corresponding to advantageous effects of the configurations described later in the embodiments as other problems.

An X-ray CT apparatus according to an embodiment includes a gantry. The gantry includes: a rotating base that is rotatably supported; a plurality of units fixed to the rotating base; and a fixing member that is separately provided, is positioned apart from the rotating base, and is configured to fix at least two of the plurality of units with each other.

Exemplary embodiments of an X-ray CT apparatus and an attaching method and a detaching method of units within a gantry of an X-ray CT apparatus will be explained in detail below, with reference to the accompanying drawings. Further, possible embodiments of the X-ray CT apparatus and the attaching method and the detaching method of the units within the gantry of the X-ray CT apparatus are not limited to the embodiments described below. Also, it is possible to combine any of the embodiments with another embodiment or a conventional technique as long as no conflict occurs among the configurations. Furthermore, in the following explanations, some of the constituent elements that are the same as each other will be referred to by using the same reference characters, and duplicate explanations thereof may be omitted.

First Embodiment

FIG. 1 is a diagram illustrating an exemplary configuration of an X-ray CT apparatus 1 according to a first embodiment. As illustrated in FIG. 1, the X-ray CT apparatus 1 according to the first embodiment includes a gantry device 10, a table device 30, and a console device 40.

In FIG. 1, the rotation axis of a rotating frame 13 in a non-tilted state or the longitudinal direction of a tabletop 33 of the table device 30 is defined as a Z-axis direction. The Z-axis direction is an example of the scan axis direction. Further, an axial direction orthogonal to the Z-axis direction and parallel to a floor surface is defined as an X-axis direction. In addition, an axial direction orthogonal to the Z-axis direction and to the X-axis direction and perpendicular to the floor surface is defined as a Y-axis direction. Although FIG. 1 depicts the gantry device 10 from multiple directions for the sake of explanations, the X-ray CT apparatus 1 includes the single gantry device 10 in the depicted example.

The gantry device 10 includes an X-ray tube 11, an X-ray detector 12, the rotating frame 13, an X-ray high-voltage device 14, a controlling device 15, a wedge 16, a collimator 17, and a Data Acquisition System (DAS) 18. The gantry device 10 may be referred to as a gantry.

The X-ray tube 11 is a vacuum tube having a negative pole (a filament) configured to generate thermo electrons and a positive pole (a target or an anode) configured to generate X-rays in response to collision of the thermo electrons thereon. The X-ray tube 11 is configured to generate X-rays to be radiated onto an examined subject (hereinafter, "patient") P, by emitting the thermo electrons from the negative pole toward the positive pole, with high voltage applied from the X-ray high-voltage device 14. Examples of the X-ray tube 11 include an X-ray tube of a rotating anode type configured to generate X-rays by emitting thermo electrons onto a rotating positive pole (anode).

The X-ray detector 12 is configured to detect X-rays that were emitted from the X-ray tube 11 and have passed through the patient P and is configured to output a signal corresponding to the amount of the detected X-rays to the DAS 18. For example, the X-ray detector 12 includes a plurality of rows of detecting elements in each of which a plurality of detecting elements are arranged in a channel direction along an arc centered on a focal point of the X-ray tube 11. For example, the X-ray detector 12 has a structure in which the plurality of rows of detecting elements are arranged in a row direction (i.e., a slice direction), while each of the rows includes a plurality of detecting elements arranged in the channel direction.

For example, the X-ray detector 12 is a detector of an indirect conversion type including a grid, a scintillator array, and an optical sensor array. The scintillator array includes a plurality of scintillators. Each of the scintillators includes a scintillator crystal that outputs light in a photon quantity corresponding to the amount of incident X-rays. The grid is arranged on a surface of the scintillator array that is positioned on the X-ray incident side and includes an X-ray blocking plate configured to absorb scattered X-rays. The grid may be referred to as a collimator (a one-dimensional collimator or a two-dimensional collimator) in some situations. The optical sensor array has a function of converting the photon quantities of the light from the scintillators into corresponding electrical signals and includes an optical sensor using a photodiode or the like, for example. Alternatively, the X-ray detector 12 may be a detector of a direct conversion type that includes a semiconductor element configured to convert incident X-rays into an electrical signal.

The rotating frame 13 is an annular frame configured to support the X-ray tube 11 and the X-ray detector 12 so as to oppose each other and configured to rotate the X-ray tube 11 and the X-ray detector 12 via the controlling device 15. For example, the rotating frame 13 is cast by using aluminum as a material thereof. In addition to the X-ray tube 11 and the X-ray detector 12, the rotating frame 13 is also capable of further supporting the X-ray high-voltage device 14, the wedge 16, the collimator 17, the DAS 18, and the like. Furthermore, the rotating frame 13 is also capable of further supporting various types of elements that are not illustrated in FIG. 1. The various types of elements supported by the rotating frame 13 will be explained later. The rotating frame 13 may be referred to as a rotating base or a rotating member. Further, in the gantry device 10, the rotating frame 13 and a part that rotates and moves together with the rotating frame 13 may be referred to as a rotating part.

The X-ray high-voltage device 14 includes: a high-voltage generating device including electrical circuits such as a transformer, a rectifier, and the like and being configured to generate the high voltage to be applied to the X-ray tube 11; and an X-ray controlling device configured to control output voltage corresponding to the X-rays to be generated by the X-ray tube 11. The high-voltage generating device may be of a transformer type or an inverter type. Further, the X-ray high-voltage device 14 may be provided on the rotating frame 13 or may be provided on a fixed frame (not illustrated).

The controlling device 15 includes a processing circuit having a Central Processing Unit (CPU) or the like and a driving mechanism such as a motor and an actuator. The controlling device 15 is configured to control operations of the gantry device 10 and the table device 30, upon receipt of input signals from an input interface 43. For example, the controlling device 15 is configured to exercise control over the rotation of the rotating frame 13, tilting of the gantry device 10, operations of the table device 30 and the tabletop 33, and the like. In an example, the controlling device 15 is provided with a rotation driving device 52 (see FIG. 2A) including a bearing, a motor, and the like for rotating the rotating frame 13. The rotation driving device 52 of the controlling device 15 is configured to rotate the rotating frame 13 on a rotation axis, which is an axis parallel to the Z-axis direction. In this situation, the controlling device 15 may be provided for the gantry device 10 or may be provided for the console device 40.

The wedge 16 is a filter for adjusting the amount of the X-rays emitted from the X-ray tube 11. More specifically, the wedge 16 is a filter configured to pass and attenuate the X-rays emitted from the X-ray tube 11, so that the X-rays emitted from the X-ray tube 11 onto the patient P has a predetermined distribution. The wedge 16 may be a wedge filter or a bow-tie filter, for example, and is a filter obtained by processing aluminum or the like so as to have a predetermined target angle and a predetermined thickness.

The collimator 17 is structured with lead plates or the like for narrowing down the radiation range of the X-rays that have passed through the wedge 16 and is configured to form slits with a combination of the plurality of lead plates or the like. Further, the collimator 17 may be referred to as an X-ray limiter. Although FIG. 1 illustrates an example in which the wedge 16 is provided between the X-ray tube 11 and the collimator 17, another example is also acceptable in which the collimator 17 is provided between the X-ray tube 11 and the wedge 16. In that situation, the wedge 16 is configured to pass and attenuate the X-rays which are emitted from the X-ray tube 11 and of which the radiation range has been limited by the collimator 17.

The DAS 18 is configured to acquire signals of the X-rays detected by the detecting elements included in the X-ray detector 12. For example, the DAS 18 includes an amplifier that performs an amplifying process on the electrical signals output from the detecting elements and an Analog/Digital (A/D) converter that converts the electrical signals into digital signals and is configured to generate detection data.

The data generated by the DAS 18 is transmitted via optical communication, from a transmitter provided on the rotating frame 13 and including a Light Emitting Diode (LED), to a receiver provided in a non-rotating part (e.g., the fixed frame; not illustrated in FIG. 1) of the gantry device 10 and including a photodiode, so as to be further transferred to the console device 40. In this situation, the non-rotating part may be, for example, the fixed frame or the like configured to rotatably support the rotating frame 13. Further, possible methods for transmitting the data from the rotating frame 13 to the non-rotating part of the gantry device 10 are not limited to the optical communication. It is acceptable to adopt any contactless data transfer method or to adopt a contact-type data transfer method.

The table device 30 is a device on which the patient P to be imaged is placed and moved and includes a base 31, a table driving device 32, the tabletop 33, and a supporting frame 34. The base 31 is a casing configured to movably support the supporting frame 34 in vertical directions. The table driving device 32 is a driving mechanism configured to move the tabletop 33 on which the patient P is placed, in the long-axis directions of the tabletop 33 and includes a motor and an actuator or the like. The tabletop 33 provided on the top face of the supporting frame 34 is a board on which the patient P is placed. In addition to moving the tabletop 33, the table driving device 32 may also be configured to move the supporting frame 34 in the long-axis directions of the tabletop 33.

The console device 40 includes a memory 41, a display 42, an input interface 43, and a processing circuit 44. Further, although an example is explained in which the console device 40 and the gantry device 10 are separate from each other, the gantry device 10 may include the console device 40 or a part of the constituent elements of the console device 40.

The memory 41 is realized by using, for example, a semiconductor memory element such a Random Access Memory (RAM) or a flash memory, or a hard disk, an optical disk, or the like. For example, the memory 41 is configured to store therein projection data and CT image data. Further, for example, the memory 41 is configured to store therein a program used by circuits included in the X-ray CT apparatus 1 for realizing various types of functions. It is also acceptable to realize the memory 41 by using a group of servers (a cloud) connected to the X-ray CT apparatus 1 via a network.

The display 42 is configured to display various types of information. For example, the display 42 is configured to display various types of images generated by the processing circuit 44 and to display a Graphical User Interface (GUI) used for receiving various types of operations from an operator. For example, the display 42 may be a Liquid Crystal Display (LCD) or a Cathode Ray Tube (CRT) display. The display 42 may be of a desktop type or may be configured by using a tablet terminal or the like capable of wirelessly communicating with the main body of the console device 40. Further, the display 42 is an example of a display unit.

The input interface 43 is configured to receive various types of input operations from the operator, to convert the received input operations into electrical signals, and to output the electrical signals to the processing circuit 44. Further, for example, the input interface 43 is configured to receive, from the operator, operation to input a scan condition, a reconstruction condition used at the time of reconstructing the CT image data, an image processing condition used at the time of generating a post-processing image from the CT image data, and the like.

For example, the input interface 43 is realized by using a mouse, a keyboard, a trackball, a switch, a button, a joystick, a touchpad on which input operations can be performed by touching an operation surface thereof, a touch screen in which a display screen and a touchpad are integrally formed, a contactless input circuit using an optical sensor, an audio input circuit, and/or the like. In this situation, the input interface 43 may be provided for the gantry device 10. Further, the input interface 43 may be configured by using a tablet terminal or the like capable of wirelessly communicating with the main body of the console device 40. Further, the input interface 43 does not necessarily have to include physical operation components such as a mouse, a keyboard and/or the like. For instance, possible examples of the input interface 43 include an electrical signal processing circuit configured to receive an electrical signal corresponding to an input operation from an external input device provided separately from the console device 40 and to output the electrical signal to the processing circuit 44.

The processing circuit 44 is configured to control operations of the entirety of the X-ray CT apparatus 1. For example, the processing circuit 44 is configured to implement a controlling function 441, a pre-processing function 442, a reconstruction processing function 443, and an image processing function 444. In this situation, for example, processing functions executed by the constituent elements of the processing circuit 44 illustrated in FIG. 1, namely, the controlling function 441, the pre-processing function 442, the reconstruction processing function 443, and the image processing function 444 are recorded in the memory 41 in the form of computer-executable programs. For example, the processing circuit 44 is a processor and is configured to read and execute the programs from the memory 41 so as to realize the functions corresponding to the read programs. In other words, the processing circuit 44 that has read the programs has the function illustrated within the processing circuit 44 in FIG. 1.

Although FIG. 1 illustrates the example in which the processing functions such as the controlling function 441, the pre-processing function 442, the reconstruction processing function 443, and the image processing function 444 are realized by the single processing circuit (i.e., the processing circuit 44), possible embodiments are not limited to this example. For instance, it is also acceptable to structure the processing circuit 44 by combining together a plurality of independent processors, so that the processing functions are realized as a result of the processors executing the programs. Further, the processing functions included in the processing circuit 44 may be realized as being distributed among or integrated into one or more processing circuits, as appropriate.

The controlling function 441 is configured to control various types of processes on the basis of the input operations received from the operator via the input interface 43. More specifically, the controlling function 441 is configured to control a CT scan performed by the gantry device 10. For example, the controlling function 441 is configured to control a counting result acquisition process performed by the gantry device 10, by controlling operations of the X-ray high-voltage device 14, the X-ray detector 12, the controlling device 15, the DAS 18, and the table driving device 32. In one example, the controlling function 441 is configured to control each of the projection data acquisition processes in a position determining scan performed to acquire a position determining image (a scanogram image) and in an imaging process (a main scan) performed to acquire an image to be used for a diagnosing process.

Further, the controlling function 441 is configured to cause the display 42 to display images based on various types of image data stored in the memory 41, and the like.

The pre-processing function 442 is configured to generate the projection data by performing pre-processing processes such as a logarithmic conversion process, an offset correcting process, an inter-channel sensitivity correcting process, a beam hardening correction, a scattered ray correction, a dark count correction, and/or the like, on the detection data output from the DAS 18. In this situation, the data obtained by performing the pre-processing processes on the detection data may be referred to as raw data. In contrast, the detection data before performing the pre-processing processes and the raw data resulting from the pre-processing processes may be referred to as projection data.

The reconstruction processing function 443 is configured to generate the CT image data by performing a reconstructing process using a filtered backprojection method, a successive approximation reconstruction method, or the like, on the projection data generated by the pre-processing function 442. The reconstruction processing function 443 is configured to store the reconstructed CT image data into the memory 41.

On the basis of the input operations received from the operator via the input interface 43, the image processing function 444 is configured to convert the CT image data generated by the reconstruction processing function 443, into image data of a cross-sectional image on an arbitrary cross-sectional plane or of a three-dimensional image resulting from a rendering process, by using a publicly-known method. The image processing function 444 is configured to store the image data resulting from the conversion into the memory 41.

The configuration of the X-ray CT apparatus 1 according to the first embodiment has thus been explained. The X-ray CT apparatus 1 structured as described above is configured to perform the processes described below, so as to be able to reduce the weight and increase the rigidity of the entirety of the rotating part including the rotating frame 13.

Figure 2A:
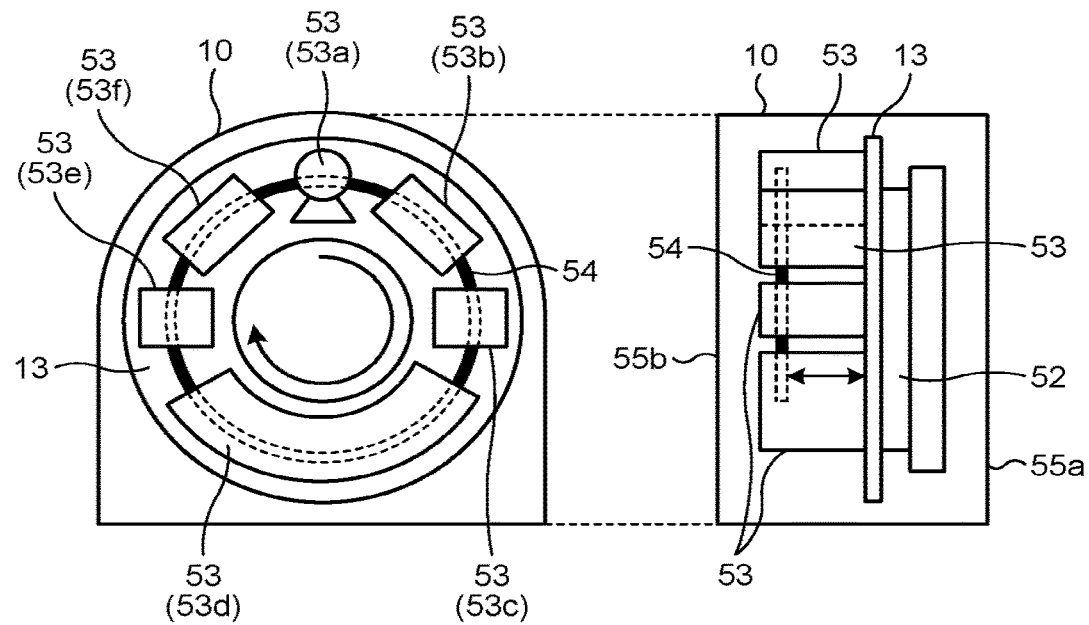
FIG. 2A is a diagram illustrating an exemplary configuration of a gantry device according to the first embodiment.
Figure 2B:
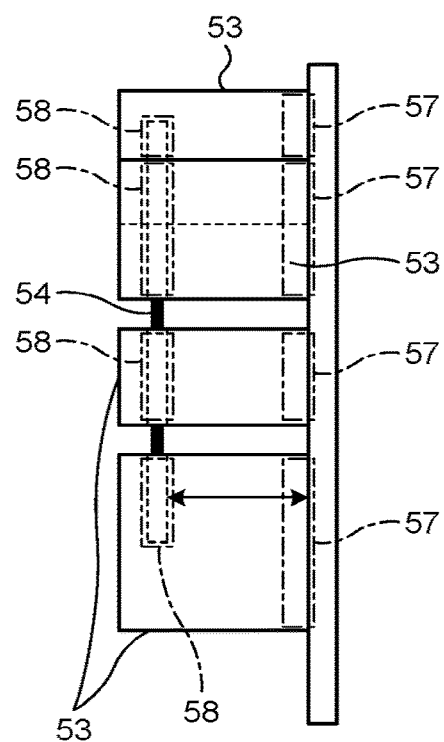
FIG. 2B is a diagram illustrating a detailed exemplary configuration of a part of the gantry device according to the first embodiment.

FIG. 2A is a diagram illustrating an exemplary configuration of the gantry device 10 according to the first embodiment. FIG. 2B is a diagram illustrating a detailed exemplary configuration of a part of the gantry device 10 according to the first embodiment. The left-hand side of FIG. 2A illustrates an example of an internal structure of the gantry device 10 in an X-Y planar view. The right-hand side of FIG. 2A illustrates an example of the internal structure of the gantry device 10 in a Z-Y planar view.

As illustrated in FIG. 2A, the gantry device 10 includes a cover, the rotating frame 13, the rotation driving device 52, a plurality of units (six units in the example in FIG. 2A) 53, and a cross member 54.

The cover of the gantry device 10 is configured to house therein the rotating frame 13, the rotation driving device 52, the plurality of units 53, and the cross member 54. The cover of the gantry device 10 is formed by using reinforced resin such as Fiber Reinforced Plastic (FRP), for example. The cover of the gantry device 10 includes a first cover 55a and a second cover 55b. Within the entire region of the rotating part, the first cover 55a is provided so as to cover a region positioned on the rotation driving device 52 side. The second cover 55b is provided so as to be able to open and close on the first cover 55a. For example, while the second cover 55b is closed on the first cover 55a, the second cover 55b is provided so as to cover a region positioned on the units 53 side, within the entire region of the rotating part. The second cover 55b is opened at the time of attaching the units 53 to the rotating frame 13, at the time of attaching the cross member 54 to the units 53, at the time of detaching the cross member 54 from the units 53, and at the time of detaching the units 53 from the rotating frame 13.

As explained above, the rotating frame 13 is rotatably supported by the fixed frame or the like. For example, the rotating frame 13 is configured to rotate on a plane parallel to the X-Y plane, while using an axis extending parallel to the Z-axis direction as a rotation axis. The rotating frame 13 has a lateral face and two main faces and is structured with an annular member obtained by forming a hole in a central part of each of the two main faces. In other words, the rotating frame 13 according to the present embodiment has an annular shape, and not a circular cylindrical shape. The rotating frame 13 is cast by using aluminum as a material thereof, for example. As illustrated in FIG. 2A, the plurality of units 53 are fixed to one of the two main faces of the rotating frame 13. Further, the rotation driving device 52 is provided on the side of the other of the two main faces of the rotating frame 13.

The plurality of units 53 are the X-ray tube 11, the X-ray high-voltage device 14, the X-ray detector 12, and the like, described above. Alternatively, the plurality of units 53 may include a starter unit for rotating the positive pole of the X-ray tube 11 or a heat exchanger (a cooling device) for the X-ray tube 11. When the plurality of units 53 are individually distinguished from one another, reference characters 53a to 53f are assigned to the units in place of the reference numeral 53. For example, the unit 53a denotes the X-ray tube 11; the unit 53b denotes the heat exchanger for the X-ray tube 11; the unit 53c denotes the starter unit; the unit 53d denotes the X-ray detector 12; the unit 53e denotes an inverter unit for the X-ray high-voltage device 14; and the unit 53f denotes a voltage boosting element for the X-ray high-voltage device 14.

Figure 3:
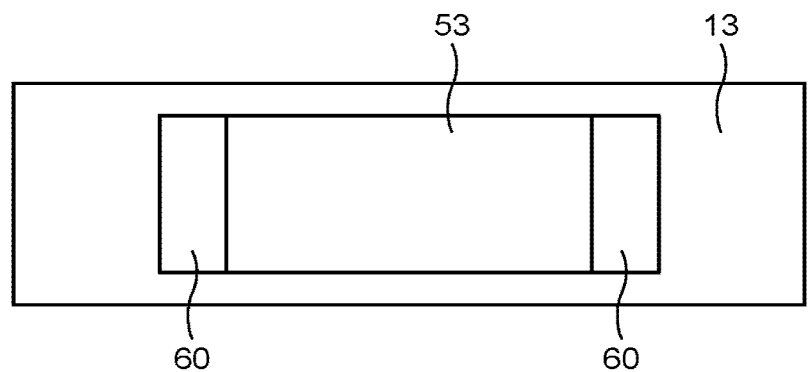
FIG. 3 is a diagram for explaining an example of a method for fixing units to a rotating frame according to the first embodiment.

The plurality of units 53 are fixed to the rotating frame 13. More specifically, as explained above, the plurality of units 53 are fixed to the one of the two main faces of the rotating frame 13. FIG. 3 is a diagram for explaining an example of a method for fixing the units 53 to the rotating frame 13 according to the first embodiment.

Among the plurality of units 53, the unit 53d, which is the X-ray detector 12, is attached by being fixed to a beam projecting from one of the main faces of the rotating frame 13. In contrast, the rest of the units 53 are attached, as illustrated in FIG. 3, by being fixed to the one of the main faces of the rotating frame 13 via a bracket 60. In the following sections, the main face of the rotating frame 13 to which the units 53 are fixed will be referred to as an "attachment face".

The bracket 60 is an L-shaped member and formed by bending a slender plate-like member by approximately 90 degrees. In other words, the bracket 60 is structured with: a first slender plate-like member; and a second slender plate-like member extending in a direction that intersects the extending direction of the first plate-like member at approximately 90 degrees.

Of the bracket 60, the first plate-like member is attached to the units 53. Accordingly, the bracket 60 is attached to the units 53 in such a manner that the second plate-like member of the bracket 60 projects from the units 53. Further, the bracket 60 is fixed onto the attachment face in such a manner that, of the two main faces of the second plate-like member of the bracket 60, the main face positioned on the attachment face side of the rotating frame 13 is fitted along the attachment face. More specifically, the one of the main faces of the second plate-like member of the bracket 60 positioned on the attachment face side is fixed with the attachment face of the rotating frame 13 by fixing members (fastening members) such as a bolt and a nut. As a result, the units 53 are fixed by being attached to the rotating frame 13 via the bracket 60. In this situation, the bolt is an example of the first fixing member inserted in the Z-axis direction.

When attaching the units 53 onto the rotating frame 13, the user attaches and fixes the units 53 onto the rotating frame 13 by opening the second cover 55b and using the method described above that uses the fixing members such as the bolt and the nut.

Further, when detaching the units 53 from the rotating frame 13, the user detaches the units 53 from the rotating frame 13, by opening the second cover 55b and pulling out the fixing members.

The fixing members such as the bolt and the nut are visually recognized as being exposed, when the user views in the Z-axis direction while the second cover 55b is open. For this reason, the user is able to easily insert and pull out the fixing members such as the bolt and the nut in the Z-axis direction, by opening the second cover 55b. Accordingly, in the present embodiment, the user is able to attach the units 53 onto the rotating frame 13 and to detach the units 53 from the rotating frame 13 easily.

The cross member 54 is an annular member. For example, the cross member 54 may be cast by using metal such as aluminum as a material thereof. However, as long as a high level of strength is achieved, the cross member 54 does not necessarily have to be cast. The cross member 54 is configured to fasten the plurality of units 53 firmly by joining the plurality of units 53 together. In other words, the cross member 54 is configured to fix the plurality of units 53 with one another.

Figure 4:
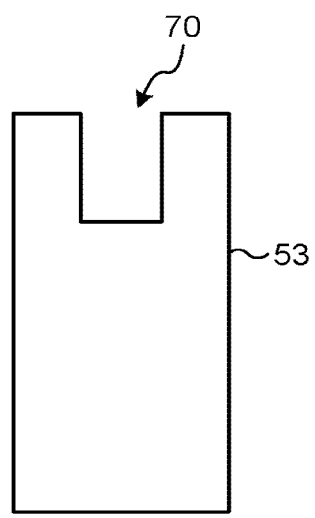
FIG. 4 is a diagram illustrating an exemplary configuration of any one of the units according to the first embodiment.

FIG. 4 is a diagram illustrating an exemplary configuration of any one of the units 53 according to the first embodiment. As illustrated in FIG. 4, each of the plurality of units 53 has a groove 70 formed therein. More specifically, on the face of the unit 53 positioned opposite from the face on the rotating frame 13 side, the groove 70 shaped to match the shape of the cross member 54 is formed so that the cross member 54 can be fitted therein.

By being fitted into the grooves 70 formed in the plurality of units 53, the cross member 54 is configured to fix the plurality of units 53 with one another. Because the cross member 54 has a predetermined level of rigidity, the positional relationship among the plurality of units 53 to which the cross member 54 is attached is fixed by both the rotating frame 13 and the cross member 54. In particular, in an embodiment, with respect to each of the plurality of units 53, the groove 70 is formed in the face opposite from the face that is in contact with the rotating frame 13. With this arrangement, the positional relationship of the plurality of units 53 with one another is fixed on both the contact face and the opposite face. The plurality of units 53 are thus supported and fixed on the two faces. Consequently, it is possible to realize a desired level of rigidity.

Further, as indicated by the bidirectional arrow in FIG. 2A, the cross member 54 is a separate member from the rotating frame 13 and is positioned apart from the rotating frame 13 in the Z-axis direction. More specifically, the cross member 54 is positioned apart from the rotating frame 13 in the Z-axis direction so that a gap is formed between the cross member 54 and the rotating frame 13. Next, the following will explain fixing the positional relationship among the plurality of units 53 by using the cross member 54 positioned apart from the rotating frame 13 in the Z-axis direction, with reference to FIG. 2B. For example, by using the bracket 60 (see FIG. 3), parts 57 of the plurality of units 53 positioned on the rotating frame 13 side in terms of the Z-axis direction are fixed onto the rotating frame 13. As a result, the positional relationship among the plurality of parts 57 of the plurality of units 53 positioned on the rotating frame 13 side in terms of the Z-axis direction is fixed. Further, as explained above, because the cross member 54 has the predetermined level of rigidity, the cross member 54 fixes the positional relationship among a plurality of parts 58 of the plurality of units 53 positioned on the side opposite from the rotating frame 13 in terms of the Z-axis direction. In this manner, the cross member 54 fixes the plurality of units 53, by fixing the parts 58 of the plurality of units 53 positioned on the side opposite from the parts 57 positioned on the rotating frame 13 side in terms of the Z-axis direction.

Alternatively, instead of being the annular member, the cross member 54 may be a plate-like or bar-like member or an arc-shaped member having a curved face (e.g., a member corresponding to one of four sections obtained by equally dividing, in the circumferential direction, a circular cylinder having a predetermined thickness). In that situation, the cross member 54 is configured to fix at least two of the plurality of (six) units 53 with one another. In another example, the cross member 54 may fix three or more of the plurality of (six) units 53 with one another. The cross member 54 is an example of the fixing member and the second fixing member.

When attaching the cross member 54 onto the units 53, the user attaches and fixes the cross member 54 onto the units 53, by opening the second cover 55b and pressing in the Z-axis direction so as to fit the cross member 54 into the grooves 70. In this manner, the user fixes the units 53 via the cross member 54, by pressing the cross member 54 against the units 53 in the Z-axis direction so as to be kept in contact therewith.

Further, when detaching the cross member 54 from the units 53, the user detaches the cross member 54 from the units 53, by opening the second cover 55b and pulling the cross member 54 out of the grooves 70. In that situation, the user pulls out the cross member 54 in the direction opposite from the direction in which the cross member 54 was fitted into the grooves 70.

The cross member 54 is visually recognized as being exposed, when the user views in the Z-axis direction while the second cover 55b is open. For this reason, the user is able to easily insert and pull out the cross member 54 in the Z-axis direction, by opening the second cover 55b. Accordingly, in the present embodiment, the user is able to attach the cross member 54 to the units 53 and to detach the cross member 54 from the units 53 easily.

Figure 5A:
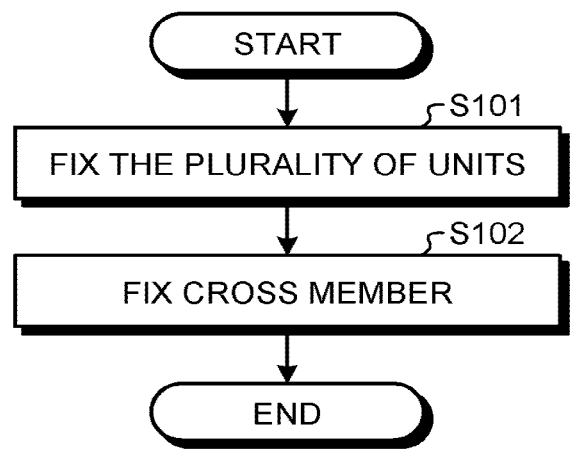
FIG. 5A is a flowchart for explaining an example of a procedure for implementing a method for attaching the units according to the first embodiment.

Next, an example of a procedure for implementing the method for attaching the units 53 within the gantry device 10 of the X-ray CT apparatus 1 will be explained. FIG. 5A is a flowchart for explaining the example of the procedure for implementing the method for attaching the units 53 according to the first embodiment. The procedure presented in FIG. 5A is performed after the user opens the second cover 55b.

As illustrated in FIG. 5A, at step S101, the user attaches and fixes the units 53 onto the rotating frame 13, by using the fixing members such as the bolt and the nut, while the second cover 55b is open.

Subsequently, at step S102, the user attaches and fixes the cross member 54 onto the units 53, by pressing in the Z-axis direction so as to fit the cross member 54 into the grooves 70, while the second cover 55b is open. As a result, the cross member 54 fixes the plurality of units 53 with one another. In this manner, the user fixes the units 53 via the cross member 54, by pressing the cross member 54 against the units 53 in the Z-axis direction so as to be kept in contact therewith.

Figure 5B:
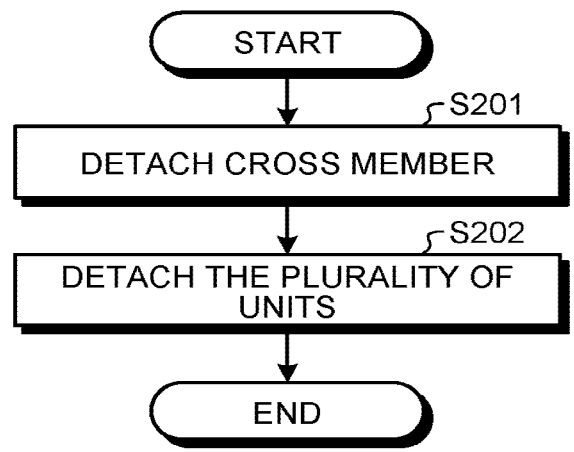
FIG. 5B is a flowchart for explaining an example of a procedure for implementing a method for detaching the units according to the first embodiment.

Next, an example of a procedure for implementing the method for detaching the units 53 within the gantry device 10 of the X-ray CT apparatus 1 will be explained. FIG. 5B is a flowchart for explaining the example of the procedure for implementing the method for detaching the units 53 according to the first embodiment. The procedure presented in FIG. 5B is performed after the user opens the second cover 55b.

As illustrated in FIG. 5B, at step S201, the user detaches the cross member 54 from the units 53, by pulling the cross member 54 out of the grooves 70 in the direction opposite from the direction in which the cross member 54 was fitted into the grooves 70, while the second cover 55b is open.

Subsequently, at step S202, the user detaches the units 53 from the rotating frame 13, by pulling out the fixing members such as the bolt and the nut, while the second cover 55b is open.

The X-ray CT apparatus 1 according to the first embodiment has thus been explained. In the first embodiment, the rotating frame 13, the plurality of units 53, and the cross member 54 are realized as an integrally-formed rotating structure. Accordingly, the rotating part including the rotating structure has high rigidity while making use of the mechanical strength of the units 53. Further, the rotating part is lightweight. With the first embodiment, it is possible to realize the reduced weight and the increased rigidity of the entirety of the rotating part including the rotating frame 13.

Further, because the weight of the entirety of the rotating part is successfully reduced, it is possible to lower the electric energy required to rotate the rotating frame 13.

In addition, as explained above, the cross member 54 is provided so as to be positioned apart from the rotating frame 13 in the Z-axis direction, so that the gap is formed between the cross member 54 and the rotating frame 13. Accordingly, in the first embodiment, air flows more easily from the rotation center of the rotating part toward the outer circumference, in comparison to the example of a conventional drum-shaped rotating base with which no such gap provided. Consequently, according to the first embodiment, it is possible to release heat easily and to thus cool the rotating part more efficiently. Further, as a result, because the air flow within the gantry device 10 is improved, it is possible to reduce noise that may be caused by stagnation of the air. In addition, because heat releasability is improved, it is possible to reduce the use of a fan for heat releasing purposes, which in turn reduces noise made by the fan.

Second Embodiment

In the first embodiment, the example was explained in which the annular- or arc-shaped cross member 54 is used. However, the cross member may have a polygonal shape. Thus, this embodiment will be explained as a second embodiment. In the description of the second embodiment, differences from the first embodiment will primarily be explained. Explanations of some of the elements that are the same as those in the first embodiment may be omitted.

Figure 6:
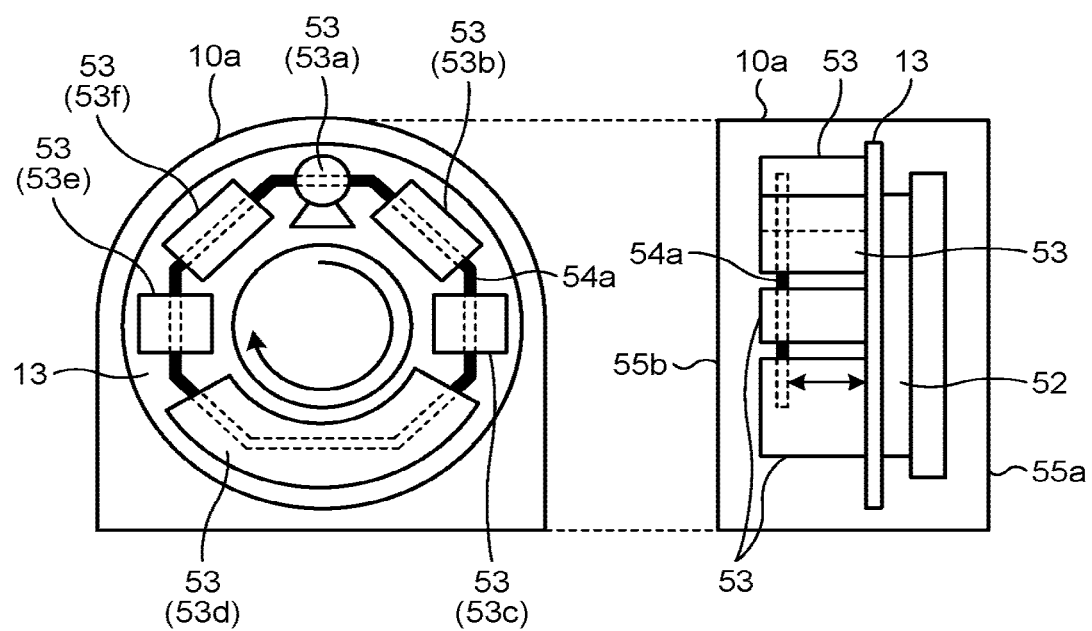
FIG. 6 is a diagram illustrating an exemplary configuration of a gantry device according to a second embodiment.

FIG. 6 is a diagram illustrating an exemplary configuration of a gantry device 10a according to the second embodiment. An X-ray CT apparatus according to the second embodiment is different from the X-ray CT apparatus 1 according to the first embodiment for including the gantry device 10a in place of the gantry device 10.

The gantry device 10a is different from the gantry device 10 according to the first embodiment for including a cross member 54a in place of the cross member 54. As illustrated in FIG. 6, the cross member 54a has an octagonal shape, because the quantity of the units 53 to be fixed by the cross member 54a is eight. In other words, in the second embodiment, for example, when the quantity of the units 53 to be fixed by the cross member 54a is W (where W is an integer of 3 or larger), the cross member 54a is shaped as a polygon having W sides. Further, when the quantity of the units 53 to be fixed by the cross member 54a is two, the cross member 54a is shaped as a bar-like member bent in one location thereof. The cross member 54a is an example of the fixing member and the second fixing member.

The X-ray CT apparatus according to the second embodiment has thus been explained. With the second embodiment, it is possible to achieve the same advantageous effects as those of the first embodiment.

Third Embodiment

It is possible to configure the cross member 54 according to the first embodiment or the cross member 54a according to the second embodiment so as to be provided on the inner face of the second cover 55b so that, when the second cover 55b is closed, the cross member 54 or the cross member 54a fixes the plurality of units 53. Thus, this embodiment will be explained as a third embodiment. In the description of the third embodiment, differences from the first embodiment or the second embodiment will primarily be explained. Explanations of some of the elements that are the same as those in the first embodiment or the second embodiment may be omitted.

Figure 7A:
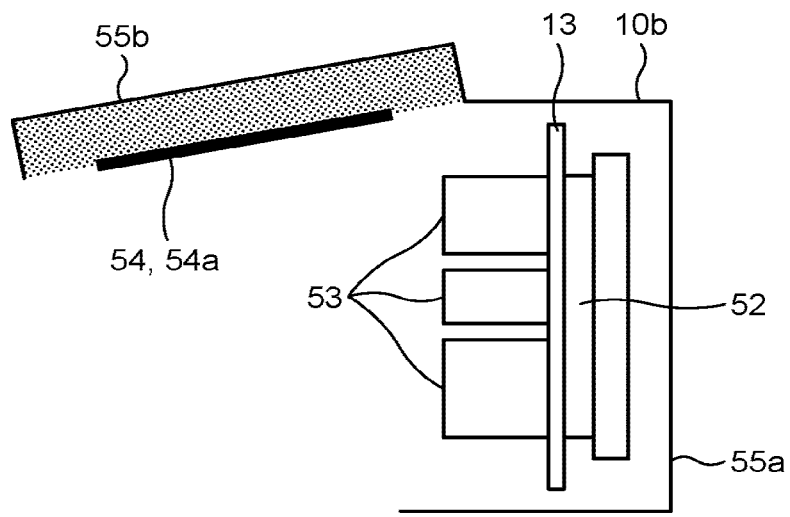
FIG. 7A is a diagram illustrating an exemplary configuration of a gantry device while a second cover is open according to a third embodiment.
Figure 7B:
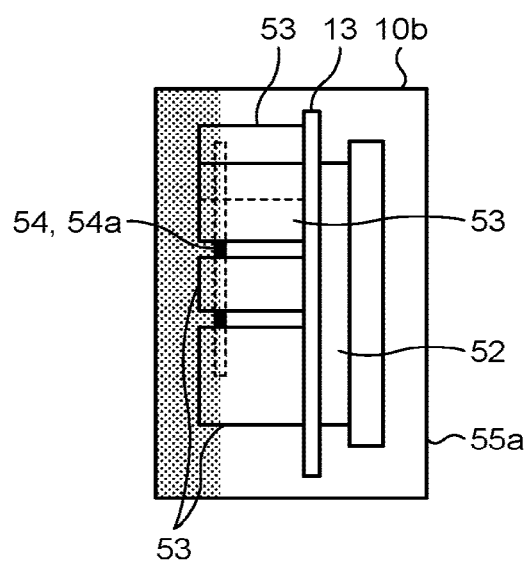
FIG. 7B is a diagram illustrating an exemplary configuration of the gantry device while the second cover is closed according to the third embodiment.

FIGS. 7A and 7B are diagrams illustrating an exemplary configuration of a gantry device 10b according to the third embodiment. An X-ray CT apparatus according to the third embodiment is different from the X-ray CT apparatus 1 according to the first embodiment and the X-ray CT apparatus according to the second embodiment for including the gantry device 10b in place of the gantry devices 10 and 10a.

FIG. 7A illustrates the situation where the second cover 55b is open, whereas FIG. 7B illustrates the situation where the second cover 55b is closed. In the gantry device 10b, the cross member 54 or the cross member 54a is rotatably supported by the inner face of the second cover 55b. For example, to the second cover 55b, the cross member 54 or the cross member 54a is attached via a bearing. For example, while the second cover 55b is closed as illustrated in FIG. 7B, the second cover 55b supports the cross member 54 or the cross member 54a, in such a manner that the cross member 54 or the cross member 54a is rotatable along the X-Y plane.

Further, while the second cover 55b is closed as illustrated in FIG. 7B, the cross member 54 or the cross member 54a is attached and fixed onto the plurality of units 53. With this configuration, according to the third embodiment, the user is able to attach the cross member 54 or 54a to the units 53 with the simple operation of closing the second cover 55b. Consequently, the user is able to easily attach the cross member 54 or 54a to the units 53.

Further, with the simple operation of opening the second cover 55b, the user is able to detach the cross member 54 or 54a from the units 53. Consequently, the user is able to easily detach the cross member 54 or 54a from the units 53.

The X-ray CT apparatus according to the third embodiment has thus been explained. According to the third embodiment, as explained above, the user is able to easily attach the cross member 54 or 54a to the units 53. Further, with the third embodiment, it is possible to achieve the same advantageous effects as those of the first embodiment and the second embodiment.

Fourth Embodiment

In the first to the third embodiments, the examples were explained in which the single cross member 54 or 54a having an annular shape or an arc shape is used. However, it is also acceptable to use multiple cross members. Thus, this embodiment will be explained as a fourth embodiment. In the description of the fourth embodiment, differences from any of the first to the third embodiments will primarily be explained. Explanations of some of the elements that are the same as those in any of the first to the third embodiments may be omitted.

Figure 8:
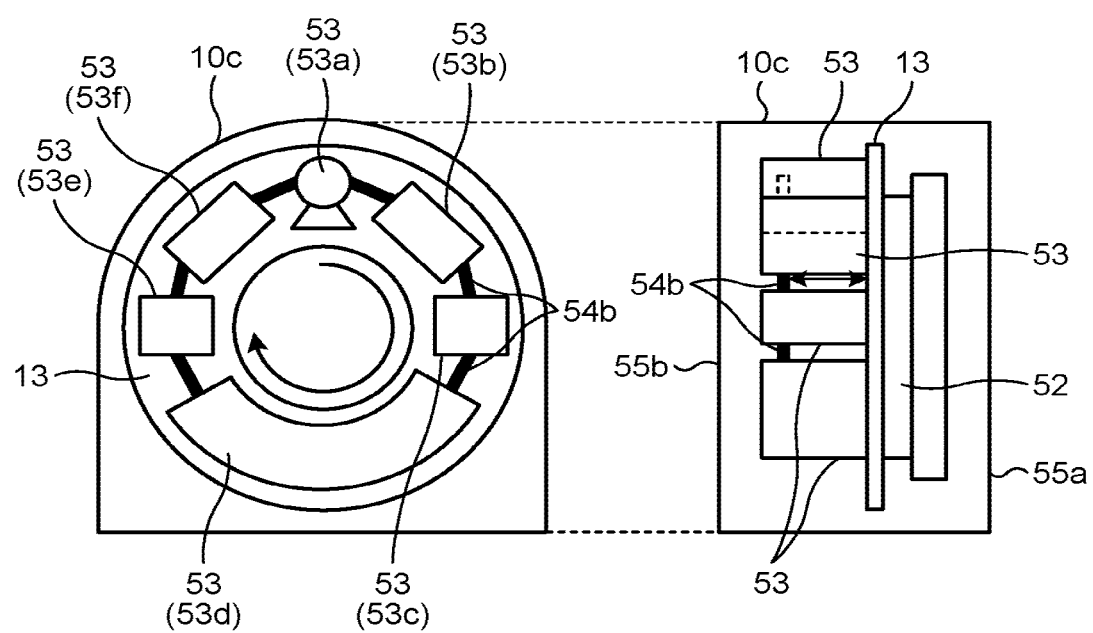
FIG. 8 is a diagram illustrating an exemplary configuration of a gantry device according to a fourth embodiment.

FIG. 8 is a diagram illustrating an exemplary configuration of a gantry device 10c according to a fourth embodiment. An X-ray CT apparatus according to the fourth embodiment is different from the X-ray CT apparatus 1 according to the first embodiment for including the gantry device 10c in place of the gantry device 10.

The gantry device 10c is different from the gantry device 10 according to the first embodiment for including a plurality of cross members 54b, in place of the cross member 54. As illustrated in FIG. 8, the gantry device 10c includes six cross members 54b, because the quantity of the units 53 to be fixed by the cross members 54b is six. In other words, in the fourth embodiment, for example, when the quantity of the units 53 to be fixed by all the cross member 54b is W (where W is an integer of 3 or larger), the quantity of the cross members 54b to be used is also W. Further, when the quantity of the units 53 to be fixed by all the cross members 54b is two, one or two cross members 54b are used. The cross members 54b are an example of the fixing member.

For instance, one of the six cross members 54b fixes a set made up of two units 53a and 53b with each other. Further, another one of the cross members 54b fixes another set made up of two units 53c and 53d with each other. The same applies to the other cross members 54b. The "one of the cross members 54b" is an example of the first fixing member. In the above expression, "another one of the cross members 54b" is an example of the second fixing member.

In the fourth embodiment, it is also acceptable to form a groove similar to the abovementioned groove 70 in each of the units 53 so that the cross members 54b are attached to the units 53 by being fitted into the grooves. Alternatively, the user may attach the cross members 54b to the units 53, by using sheet metal, screws, or the like.

The X-ray CT apparatus according to the fourth embodiment has thus been explained. According to the fourth embodiment, although the quantity of the cross members is larger than that in the first to the third embodiments, it is possible to reduce the mass of the cross members as a whole. Consequently, it is possible to further reduce the weight of the entirety of the rotating part including the rotating frame 13. In addition, with the fourth embodiment, it is possible to achieve the same advantageous effects as those of the first embodiment.

According to at least one aspect of the embodiments described above, it is possible to reduce the weight and increase the rigidity of the entirety of the rotating part including the rotating frame 13.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray Computed Tomography (CT) apparatus comprising a gantry including: a rotating base rotatably supported; a plurality of units fixed to the rotating base; and a fixing member that is separately provided, is positioned apart from the rotating base, and is configured to fix at least two of the plurality of units with each other.

2. The X-ray CT apparatus according to claim 1, wherein
the rotating base is structured with an annular member that has a hole formed in a central part thereof and has a lateral face and two main faces, and
said at least two of the units are fixed to one of the two main faces.

3. The X-ray CT apparatus according to claim 2, wherein the fixing member is configured to fix a part of each of said at least two of the units positioned opposite from a part positioned on the rotating base side.

4. The X-ray CT apparatus according to claim 1, wherein the fixing member is configured to fix three or more of the plurality of units with one another.

5. The X-ray CT apparatus according to claim 1, wherein the fixing member includes: a first fixing member configured to fix a set made up of two of the plurality of units with each other; and a second fixing member configured to fix another set made up of two other units from the plurality of units with each other.

6. The X-ray CT apparatus according to claim 1, wherein
the gantry further includes a cover that houses therein the rotating base, the plurality of units, and the fixing member,
the cover includes a first cover and a second cover that is able to open and close on the first cover, and
the second cover is configured to rotatably support the fixing member and has attached thereto the fixing member in such a manner that, when the second cover is closed on the first cover, the fixing member fixes said at least two of the units with each other.

7. The X-ray CT apparatus according to claim 1, wherein the fixing member is positioned apart from the rotating base, so that a gap is formed between the fixing member and the rotating base.

8. The X-ray CT apparatus according to claim 1, wherein the fixing member is configured to fix said at least two of the units by being fitted into grooves formed in said at least two of the units.

9. A method for attaching a plurality of units within a gantry of an X-ray CT apparatus, the method comprising:
a step of fixing the plurality of units onto a face of a rotating base, by using a first fixing member inserted in a scan axis direction, so as to fix, to the face of the rotating base, a bracket that is fixed while projecting from the units and that has a face extending along the face of the rotating base; and
a step of fixing, via a second fixing member, at least two of the plurality of units fixed to the rotating base, by pressing the second fixing member configured to fix said at least two of the plurality of units with each other, against said at least two of the units in the scan axis direction, so as to be kept in contact therewith.

10. The method according to claim 9, wherein
the step of fixing the bracket to the face of the rotating base by using the first fixing member is preceded by a step of opening a cover that serves as a cover of the X-ray CT apparatus and that houses therein the rotating base, the plurality of units, the bracket, the first fixing member, and the second fixing member, and
when viewed in the scan axis direction while the cover is open, the first fixing member and the second fixing member are visually recognized as being exposed.

11. A method for detaching a plurality of units within a gantry of an X-ray CT apparatus, the method comprising:
a step of detaching a second fixing member from at least two of the plurality of units fixed with each other via the second fixing member, the plurality of units being fixed to a face of a rotating base, as a result of a first fixing member inserted in a scan axis direction fixing, to the face of the rotating base, a bracket that is fixed while projecting from the units and that has a face extending along the face of the rotating base; and
a step of detaching, after the second fixing member is detached, the first fixing member from the bracket.

12. The method according to claim 11, wherein
the step of detaching the second fixing member from said at least two of the units is preceded by a step of opening a cover that serves as a cover of the X-ray CT apparatus and that houses therein the rotating base, the plurality of units, the bracket, the first fixing member, and the second fixing member, and
when viewed in the scan axis direction while the cover is open, the first fixing member and the second fixing member are visually recognized as being exposed.

* * * * *